United States Patent
Desai

(10) Patent No.: US 7,112,411 B2
(45) Date of Patent: Sep. 26, 2006

(54) DIRECT DETECTION OF BIOMOLECULES IN POLYACRYLAMIDE GEL IMPROVEMENT COMPRISING SHRINKING AND REHYDRATING OF GEL PRIOR TO LABELING

(75) Inventor: Surbhi Desai, Rockford, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 189 days.

(21) Appl. No.: 10/471,273

(22) PCT Filed: Mar. 7, 2002

(86) PCT No.: PCT/US02/06876

§ 371 (c)(1),
(2), (4) Date: Sep. 8, 2003

(87) PCT Pub. No.: WO02/073157

PCT Pub. Date: Sep. 19, 2002

(65) Prior Publication Data

US 2004/0086909 A1  May 6, 2004

Related U.S. Application Data

(60) Provisional application No. 60/274,264, filed on Mar. 8, 2001.

(51) Int. Cl.
*G07D 3/00* (2006.01)
(52) U.S. Cl. .......................................... 435/7.1; 435/4
(58) Field of Classification Search ................ 435/7.1, 435/4
See application file for complete search history.

(56) References Cited

U.S. PATENT DOCUMENTS 4,582,808 A * 4/1986 Oosawa et al. ............... 436/86
2001/0044108 A1 11/2001 Shih et al.

OTHER PUBLICATIONS

Mohamed et al. Polyacrylamide Gel Miniaturization Improves Protein Visualization and Autoradiographic Detection; Analytical Biochemistry, vol. 177, (1989) pp. 287-290.*
Bronstein et al. Clinical Applications of Luminescent Assays Foe Enzymes and Enzyme Labels; Journal of Clinical Laboratory Analysis, vol. 3, No. 5 (1989) pp. 316-322.*
Desai et al., "Direct Immunodetection of Antigens within the Precast Polyacrylamide Gel," *Analytical Biochemistry*, 297:94-98 (2001).
Mohamed et al., "Polyacrylamide Gel Miniaturization Improves Protein Visualization and Autoradiographic Detection," *Analytical Biochemistry*, 177:287-290 (1989).

* cited by examiner

*Primary Examiner*—Patricia Leith
*Assistant Examiner*—Paul C. Martin
(74) *Attorney, Agent, or Firm*—Leydig, Voit & Mayer, Ltd

(57) ABSTRACT

An improved method for detecting a target biomolecule directly in a polyacrylamide gel in which it has been separated from other substances. The improvement resides in, prior to binding the target to a probe and while the target biomolecule remains in the gel, (1) immersing the gel in a water miscible, aqueous extracting medium to shrink the gel by at least about ten percent and then (2) washing the gel with water to restore the gel to substantially its original size.

16 Claims, 2 Drawing Sheets

DIRECT DETECTION OF BIOMOLECULES IN POLYACRYLAMIDE GEL IMPROVEMENT COMPRISING SHRINKING AND REHYDRATING OF GEL PRIOR TO LABELING

FIELD OF THE INVENTION

The present invention relates to the detection of target substances and, more particularly, to detection of biomolecules directly in a gel in which they have been separated by electrophoresis.

BACKGROUND OF THE INVENTION

Capture of target substances, such as biomolecules, on solid phases has been used for years in order to facilitate their subsequent identification and to study their manner of interacting with other substances. Typical interactions are those between proteins, such as between antigens and antibodies, hormones and receptors, biotinylated molecules and biotin binding proteins, and the like. One method of capture is generally designated as "blotting," whereby the target substance is applied, directly or by transfer from another medium, to a membrane, such as nitrocellulose, polyvinylidene difluoride (PVDF), or nylon.

Blotting is most frequently used in combination with known gel electrophoresis procedures, whereby the target substance, e.g., an antigen, is first separated on a gel from other substances, typically by the electrophoresis procedure commonly referred to as SDS-PAGE (sodium dodecyl sulfate polyacrylamide gel electrophoresis). The target substance is then transferred electrophoretically to a membrane. Subsequently, the target is associated, either directly or indirectly through an intermediate primary ligand, by an affinity interaction to a reporter probe, such as an antibody, having a label attached thereto which is capable of providing a detectable signal. Radioactive, calorimetric, fluorescent, or enzymatic labels are commonly employed to provide the detectable signals which, in turn, indicate the presence and/or location of the target molecule. Responses from radioactive and fluorescent labels are generally determined directly, while the response (luminescent, fluorescent, or colorimetric) elicited with enzymatic labels is indirect in that the detectable signal results from the action of the enzyme on an appropriate substrate.

Procedures for electrophoretic separation with subsequent blotting onto a membrane have historically been referred to in the literature as either Western blotting, Northern blotting or Southern blotting. Western blotting refers to the identification of antigens as target substances, while the latter two procedures refer to identification of target RNA and DNA sequences, respectively. More recently, a variation of Western blotting, referred to as Far Western blotting, has been used to characterize protein to protein interactions, other than antigen to antibody.

A drawback associated with Western type and other blotting techniques is that they require time consuming and cumbersome steps. These include transferring the target substance from the gel to the membrane on which the substance is immobilized and then blocking the membrane. Some of these steps, particularly the transfer and immobilization operations, may be detrimental to the protein being assayed. For example, a change in antigenic nature of a protein may prevent the corresponding antibody from binding and, therefore, detecting the target molecule. Also, the pattern obtained on a membrane when a crude lysate is transferred may not be a true representation, since smaller molecular weight proteins transfer more efficiently than larger molecular weight proteins. Additionally, some proteins simply do not transfer well and, therefore, are not represented on the membrane at all.

Thus, "in gel" procedures, in which detection is accomplished without removal of the target from the gel, have distinct advantages. And, while "in gel" techniques for detection of target molecules in polyacrylamide gel were reported even before the advent of the above described blotting techniques (Burridge, K. (1976) Proc. Natl. Acad. Sci., USA, 73, 4457–4461; Rosta, J. A.; Kelly, P. T.; and Cotman, C. W. (1977) Anal. Biochem., 80, 336–376; and Olden, K. and Yamada K. M. (1977) Anal. Biochem, 78, 483–490), the procedures were very time consuming, entailing lengthy fixing, incubation and wash steps, which generally took on the order of several days. Furthermore, "in gel" techniques have heretofore been considered not sufficiently sensitive for the detection of target molecules using large reporter probes, e.g., antigen-antibody interactions. The problem encountered is to obtain sufficient penetration of the probe or primary ligand into the three-dimensional gel to achieve the required association of the target and probe to permit detection at low concentrations of target.

Accordingly, a sought after objective is to provide an efficient "in gel" detection method which is sensitive and useful for the detection of biomolecules. And, it is with respect to this objective that the present invention is directed.

SUMMARY OF THE INVENTION

In accordance with the present invention, there is provided an improvement to the method for detecting target biomolecules directly in a gel. The method to which the present improvement applies comprises separating a target biomolecule from other substances by polyacrylamide gel electrophoresis and, while the target biomolecule remains in the gel, associating it (either directly or indirectly) with a probe having a label which is capable of providing a detectable signal. The method further comprises removing any non-associated probe from the gel and detecting the presence of the target biomolecule by observing a signal attributable to the presence of the labeled probe which has remained associated with the target.

The improvement provided by the present invention resides in accomplishing the following two steps after the target molecule has been separated in the gel and prior to initiating the action(s) whereby the target biomolecule becomes associated with the probe. The first step is shrinking the gel by at least about ten percent (10%) and, preferably, at least about fifteen percent (15%). Then, in a second step, washing the gel with water for a sufficient time to restore the gel to substantially its original size. After the foregoing procedures are accomplished in accordance with this invention, the assay can be continued with the incubation, washing, and detection steps as conventionally practiced.

As is apparent, once conventional electrophoresis has been completed, utilization of the improvement provided by the present invention permits rapid completion of the assay, since there is no need for transfer to a membrane. The improved method provided by this invention can be accomplished in an elapsed time of about 30 minutes from the completion of electrophoresis to initial incubation with either primary ligand or directly with target probe. This is to be compared with typical times of at least about 2.5–3 hours needed for membrane preparation, transfer, and blocking operations associated with conventional blotting procedures. And, since there is no necessity for transferring or immobilizing the separated target molecule on a membrane, damage thereto is avoided. Quite surprisingly, the method of this invention is applicable for the direct detection in the gel of small quantities of large molecules, such as proteins.

DESCRIPTION OF THE INVENTION

Figure 1:
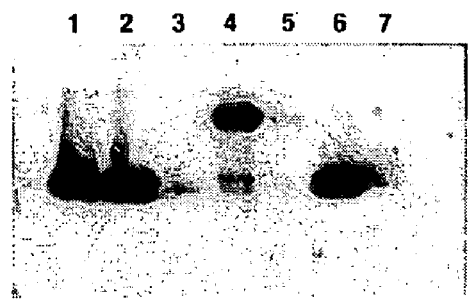
FIG. 1 shows the developed film that was exposed to the gel after completion of the assay run in Example I.

The improvement provided by the present invention is generally applicable with respect to that technique known as SDS-PAGE, wherein substances are separated by electrophoresis in an aqueous polyacrylamide gel containing sodium dodecyl sulfate. It is particularly applicable for the detection of proteinaceous biomolecules, such as antigens, antibodies, glycoproteins and other proteins. It also finds use with biotinylated and other pre-labeled molecules separated by gel electrophoresis. Once separated and identified on the gel, the protein bands in the gel can be recovered from the gel for further characterization and identification.

In view of the foregoing, the present invention provides an improved method of detecting a target biomolecule directly in a polyacrylamide gel. In a method comprising (1) separating a target biomolecule from other substances by electrophoresis in a gel, (2) associating the target biomolecule with a probe having a label which is capable of providing a detectable signal, (3) removing any non-associated probe from the gel, and (4) detecting the presence of the target biomolecule by observing a signal attributable to the presence of the labeled probe associated with the target biomolecule, the improvement comprises (A) shrinking the gel by at least 10% and then (B) washing the gel with water for a sufficient time to restore the gel to substantially its original size prior to associating the target biomolecule with the probe and while the target biomolecule remains separated in the gel.

The invention is useful in connection with probes labeled with a variety of entities as previously identified which can directly or indirectly provide a detectable signal. Conventionally, the signal is colorimetric, fluorescent or luminescent. The invention is, however, considered to be particularly useful in combination with probes containing enzymatic labels which, on contact with a substrate, produce a detectable luminescent or fluorescent signal. Horseradish peroxidase (HRP) and alkaline phosphatase are useful enzymes. When HRP is used, desirably the substrate is luminol.

A particularly preferred enzymatic detection system is described in WO97/39142, published on Oct. 23, 1997, the disclosure of which is hereby incorporated by reference in its entirety. Therein, probes containing as a label HRP are disclosed. In the presence of a luminol substrate, a source of hydrogen peroxide, and an enhancer, the HRP catalyzes an oxidation reaction which yields an intense, long-lasting luminescent signal. With use of this system in combination with the improved method of this invention, the detection, "in gel," of proteins using large target biomolecules and primary ligands is enhanced. Systems based on this luminescent technology are marketed by Pierce Chemical Company, Rockford, Ill., under the SUPERSIGNAL® trademark.

In practicing the present invention an important aspect is shrinking the gel after electrophoretic separation of the target biomolecule in the gel, but prior to initiating the incubation steps (directly with the labeled probe or indirectly first with a primary ligand) which result in achieving association of the target with the probe. To this end, the wet gel can be immersed in a water miscible, aqueous extracting medium for a sufficient time to achieve the desired shrinkage. Media comprised of water and a short-chain alcohol, such as methanol, ethanol, isopropanol, or combinations thereof, are considered most useful. Other water miscible components, in lieu of or in combination with the alcohol, such as polyethylene glycol, can be useful as well.

The alcohol in the aqueous extracting medium is present in an amount of about 10–75% v/v. Higher concentrations tend to shrink the gel excessively, resulting in embrittlement of the gel, while, at lower concentrations, inadequate shrinkage is achieved in a reasonable amount of time. The concentration of alcohol is preferably about 40–60% v/v and, more preferably, about 50% v/v. Preferably, the alcohol is methanol, ethanol, isopropanol or a combination thereof in an amount of about 35–65% v/v. More preferably, the alcohol is isopropanol in an amount of about 50% v/v. In further keeping with the present invention, the gel is maintained in the alcohol medium for a sufficient time to achieve a shrinkage of at least about 10%, based on the original surface area of the gel, preferably at least about 15%, and most preferably about 20%. Immersion for about 15 minutes is ordinarily adequate to achieve the required shrinkage. In order to minimize adverse embrittlement, shrinkage should be less than about 50%, and generally less than about 35%.

After shrinking and still in keeping with the improvement provided by this invention, the shrunk gel is washed with water, alone or as an aqueous buffer, to remove the extracting medium from the gel and, in turn, to re-hydrate the gel and restore it to substantially its original size, i.e., either the same or slightly (about 5%) smaller or larger than its original size, generally slightly larger. While any manner of washing can be employed, washing can be easily accomplished using a colander designed for gel detection procedures.

Once size restoration is accomplished by re-hydration through washing, the gel can then be directly incubated in a solution containing the labeled target probe. Alternatively, if an indirect, sandwich approach is utilized, incubation can first occur in a solution containing a primary ligand having specific affinity for the target biomolecule followed by a second incubation in a solution containing a reporter probe having affinity for the primary ligand. In either instance, the probe becomes selectively associated with the target biomolecule. At some stage during the assay procedure, sensitivity/intensity of the assay can be enhanced by sonicating the gel. Subsequent to incubation(s), the assay can be completed following conventional practice of washing and response elicitation.

Any one of many gels useful in electrophoresis applications, such as SDS-polyacrylamide, which are either commercially available or individually prepared are useful herein. The gels can be either homogeneous or gradient. Pre-cast, Tris-Glycine, Bis-Tris, Tris-Acetate and Tricine gels commercially available from Novex have been found to be particularly useful.

Furthermore, while the invention has been described with reference to one-dimensional electrophoresis, it is equally applicable with respect to the electrophoresis operation accompanying two-dimensional (2D) separations. In 2D separations, the step of gel electrophoresis is preceded by a separation of substances by isoelectric focusing. The 2D procedure is most useful when gel electrophoresis in the first dimension alone is not sufficient to separate target biomolecules.

EXAMPLES

The following examples illustrates the present invention. The reagents and materials used in the examples are as follows:

Pure glutathione-S-transferase (GST) and anti-GST, rabbit polyclonal IgG were obtained from Santa Cruz BioTechnology (Santa Cruz, Calif.). E. coli bacterial cell lysate expressing recombinant mouse Id-1:GST, mouse Id-2:GST and mouse Id-3:GST lystates were from PharMingen (San Diego, Calif.) (for general discussion of Id proteins, see, e.g., Kadesch, T. (1993) Cell Growth Differ., 4, 49–55). Mouse anti-penta-His antibody and the His tag ladder were obtained from Qiagen (Chatsworth, Calif.); LIVING COLOR™ A.v. Peptide antibody (a polyclonal antibody specific for green fluorescent protein [GFP]), rabbit, anti-6×His antibody, HRP and GFP monoclonal antibody, mouse, were from ClonTech (Palo Alto, Calif.). Tris-Glycine SDS sample buffer (2×) was obtained from Novex (San Diego, Calif.). 9H-(1,3 dichlor-9,9-dimethylacridin-2-one-7-yl)-phosphate (DDAO-phosphate) and goat anti-rabbit, alkaline phosphatase were from Molecular Probes. Enhanced chemiluminescence (ECL) was obtained from Amersham Pharmacia Biotech. The Developer/Replenisher and the Fixer/Replenisher were obtained from Sigma Chemical Corporation (St. Louis, Mo.). Gradient and homogeneous Tris-Glycine polyacrylamide gels were obtained from Novex (San Diego, Calif.). The following materials were obtained from Pierce Chemical Company (Rockford, Ill.): HRP-labeled streptavidin; Y-PER® yeast protein extraction reagent; phosphate-buffered saline (PBS); Tris-buffered saline (TBS); TWEEN® 20 surfactant; goat anti-rabbit, HRP; goat anti-mouse, HRP; electrophoresis buffer; bovine serum albumin (BSA); the stable peroxide buffer and luminal enhancer SUPERSIGNAL® West Dura Extended Duration Substrate; isopropanol; exposure film and magnesium chloride. The yeast cells and lysates (GFP & GST) and the bacterial lysate (GFP/6×His tagged) were prepared by conventional techniques. Mycobacterium Complex strain 101 (MAC 101) lysate and biotinylated human respiratory epithelial cell extract (B-Hep-2) were obtained from Dr. Venkata Reddy, School of Medicine at University of Illinois at Chicago, Rockford, Ill.

Gel sample preparation and SDS-PAGE electrophoresis were accomplished as follows. Pure protein samples were prepared by dilution in the sample buffer such that the final protein concentration was 0.1–1 ng/µl. For Example V, MAC 101 lysate was diluted so that the final concentration was from 0.5–1.5 µg/ml. Other lysate samples were diluted 1:10–1:1,000 in 2× sample buffer. All of the samples were heated at 95° C. for 5 minutes and cooled before loading onto the gels (either 4–20% or 10–20% Tris-Glycine). The samples were separated by analytical mini-gel SDS-PAGE, using Novex system, at 120 V until the dye front reached halfway down, then at 180V until the dye front reached the bottom of the gel.

The following examples, Examples I–III, illustrate the present invention in an indirect assay protocol using a primary antibody (the primary ligand) for initial bound association with the target protein followed by incubation with a labeled secondary antibody (the reporter probe), which binds to the primary antibody. Thus, the association of target and probe is indirect. Example IV illustrates the present invention in a direct assay protocol, in which the reporter probe is directly associated with the target.

Example I

The 4–20% Tris-Glycine gel (electrophoresed as described before) containing pure GST, mouse Id1:GST lysate, and yeast GST lysate was incubated for 15 min in 50 ml of 50% isopropanol/H20 to achieve about 20% shrinkage and then washed with 100 ml $H_2O$ (MILLI-Q® water) for 15 min to restore the gel to substantially its original size. The gel was incubated with 20 ml rabbit anti-GST, diluted (1:1,000) in 1% BSA/PBS/0.05% TWEEN® 20 surfactant, for 1 hr at room temperature (RT). The gel was washed 3×10 min with 100 ml PBS/0.05% TWEEN® 20 surfactant. An HRP-labeled secondary antibody [goat anti-rabbit antibody/HRP (GAR/HRP)] stock solution at 10 µg/ml was diluted 1:500 in 1% BSA/PBS/0.05% TWEEN® 20 surfactant. The diluted antibody solution (20 ml) was added to the gel. The gel was incubated for 1 hour at RT and then washed 3×10 min with 100 ml PBS/0.05% TWEEN® 20 surfactant. The gel was incubated for 5 min at RT in 10 ml of the SUPERSIGNAL® substrate working reagent. The gel was washed for 15 sec with MILLI-Q® water. The gel was placed between cellophane sheets and exposed to film for different lengths of time. The film was developed using the Developer/Replenisher and Fixer/Replenisher.

Example II

Example I was repeated except that pure GFP/6×His tagged proteins, GFP/6×His expressed in bacterial cell lysate, and GFP expressed in yeast lysate were used as targets and the primary antibody used was the rabbit anti-living color antibody. The assay took about 3.5 hrs to complete after electrophoresis. In addition, a conventional Western blot assay was run (taking about 6.5 hrs after electrophoresis) on the same target molecules, with detection being accomplished with an ECL chemiluminescent substrate from Amersham Pharmacia Biochem.

Figure 2:
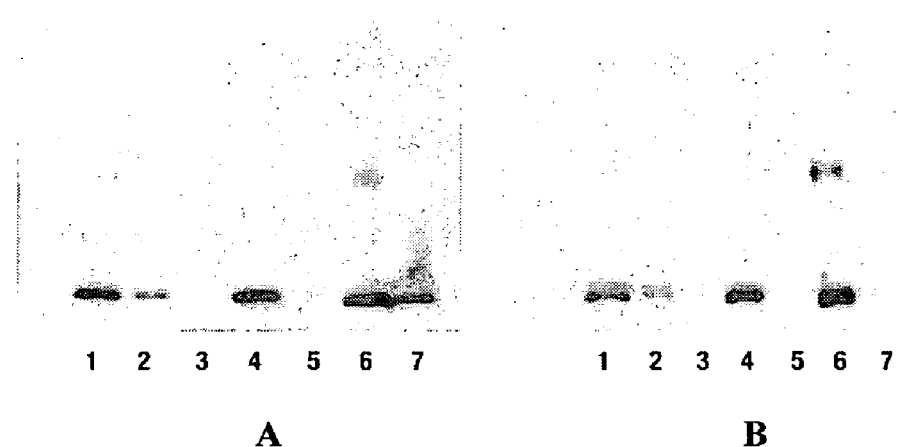
FIG. 2A shows the developed film that was exposed to the gel after completion of the assay run in Example II.
FIG. 2B shows the film that resulted from the conventional Western blot procedure.

FIG. 2 compares the "in gel" detection protocol according to the present invention (panel A) with the conventional Western Blot protocol using ECL as a detection substrate (panel B). Lanes 1, 2 and 3 correspond to 10, 5 and 1 ng pure GFP/6×His-tagged, respectively. Lanes 4 and 5 correspond to E. coli GFP/6×His-tagged lysate diluted 1:100 and 1:1,000, respectively. Lanes 6 and 7 correspond to yeast GFP lysate diluted 1:10 and 1:100, respectively. As can be seen the results are comparable but, as noted above, the time needed to complete the assay in accordance with the present invention was substantially shorter and involved less manipulative steps.

Example III

Figure 3:
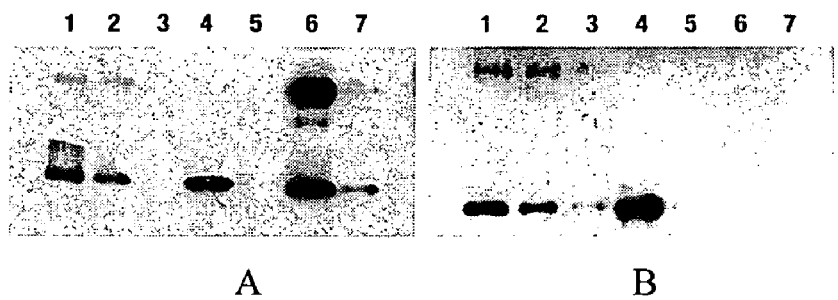
FIG. 3A shows the developed film that was exposed to the gel after completion of the assay run in Example m and probed with anti-living color primary antibody and detected with goat anti-rabbit antibody:HRP.
FIG. 3B shows the developed film that was exposed to the gel after completion of the assay run in Example m and probed with anti-penta-His primary antibody and detected with goat anti-mouse antibody:HRP.

The target proteins run in Example II in accordance with this invention were repeated except that one gel (4–20%) was probed with the same anti-living color primary antibody and detected with goat-anti rabbit antibody:HRP (FIG. 3A) and another gel probed with anti-Penta-His primary antibody (1:500 dilution) followed by goat-anti mouse antibody: HRP (1:250; 10 μg/ml) (FIG. 3B). Lanes 1, 2 and 3 correspond to 10, 5 and 1 ng pure GFP/6×His-tagged, respectively. Lanes 4 and 5 correspond to E. coli GFP/6× His-tagged lystate diluted 1:100 and 1:1,000, respectively. Lanes 6 and 7 correspond to yeast GFP lystate 1:10 and 1:100, respectively. This illustrates that detection using the instant method is specific for the antigen being probed; a specific signal is obtained in response to the primary antibody used in the assay. The Example shows that yeast GFP, which does not express a 6×His tag, is not detected by the anti-penta His antibody.

Example IV

Figure 4:
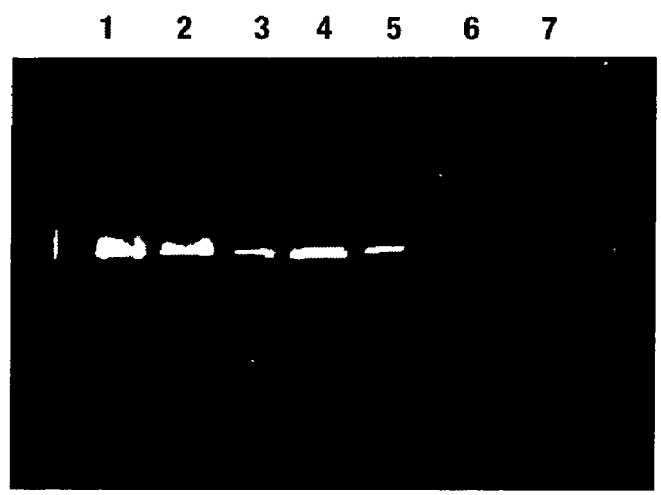
FIG. 4 shows the image capture from a CCD camera of the gel after completion of the assay run in Example IV.

The Tris-Glycine gel (10–20%), prepared as in Example II, with separated GFP/6XHis pure protein, bacterial cell lysate expressing GFP/6×His, and yeast lysate expressing GFP, was incubated for 15 min with 50 ml of 50% isopropanol/$H_2O$ and then washed with 100 ml $H_2O$ (MILLI-Q® water) for 15 min. The gel was incubated in 20 ml HRP conjugated primary antibody (anti-6×His;1:5,000), diluted in 1% BSA/PBS/0.05% TWEEN® 20 surfactant, for 1 hr at RT. The gel was washed 3×10 min with 100 ml PBS/0.05% TWEEN® 20 surfactant. The gel was then incubated for 5 min at RT in 10 ml SUPERSIGNAL® working reagent. The gel was washed for 15 sec with MILLI-Q® water. The gel was placed between cellophane sheets and exposed to an Alpha Innotech CCD camera. As shown in FIG. 4, a directly labeled primary antibody can be used in accordance with the present invention to detect antigens directly in the gel. Lanes 1, 2 and 3 correspond to 10, 5 and 1 ng pure GFP/6×His-tagged, respectively. Lanes 4 and 5 correspond to E. coli GFP/6×His-tagged lysate diluted 1:100 and 1:1,000, respectively. Lanes 6 and 7 correspond to yeast GFP lysate 1:10 and 1:100, respectively. Again, as in Example III, the antibody does not recognize the yeast GFP which does not express the His tag.

Examples V and VI illustrate the invention where the target is a protein in a cell lysate and the assay is indirect (Example V) or direct (Example VI).

Example V

An 8–16% gel was electrophoresed, as described previously, containing Mycobacterium avium complex lysate (MAC 101) diluted in sample buffer at 15, 10 and 5 μg/lane. Duplicate samples of each lysate were run on two different sides of the gel. The gel was incubated for 15 min with 50 ml of 50% isopropanol/water and then washed with 100 ml (MILLI-Q®) water for 15 min. The gel was cut in half through the middle so that each half of the gel contained the lysate samples. One of the gel halves was incubated in 20 ml biotinylated human respiratory epithelial (B-Hep-2) cell extract at a starting concentration of approximately 0.5 mg/ml and then diluted 1:200 in 1×1% BSA/PBS/05% TWEEN® 20 surfactant for 1 hr at RT. The other half was incubated in just 1% BSA/PBS/05% TWEEN® 20 surfactant for 1 hr at RT. The gel halves were washed 3×10 min with 100 ml PBS/05% TWEEN® 20 surfactant. Both gel halves were then incubated in 20 ml HRP-labeled Streptavidin solution, at 1 mg/ml, diluted 1:25,000 in 1% BSA/PBS/05% TWEEN® 20 surfactant, for 1 hr at RT. The gel halves were washed 3×10 min with 100 ml PBS/05% TWEEN® 20 surfactant. The gel halves were incubated for 5 min in 10 ml SUPERSIGNAL® substrate working reagent and then washed with MILLI-Q® water for 15 sec. The gel halves were placed in between cellophane and exposed to X-ray film for different lengths of time. The film was developed using the Developer/Replenisher and Fixer/Replenisher solutions.

A band corresponding to a 31 kD protein was observed in the gel incubated with B-Hep-2 extract. This was due to a reaction between a protein in the B-Hep-2 extract and a protein in the MAC 101 lysate. Additional endogenous biotin bands were observed in the control gel, which was not incubated with the MAC 101 lysate, and in the gel incubated with the MAC 101 lysate.

Example VI

Yeast cells ($1 \times 10^6$) were washed 3×1 ml with PBS. The cells were divided into 3 microcentifuge tubes before the last wash. PBS (100 μl) was added to each tube after the last wash. The cells in two of the tubes were biotinylated with 5 μl of NHS-LC-Biotin (at 10 mg/ml in DMF) and Sulfo-NHS-LC-Biotin (at 10 mg/ml in MILLI-Q® water) respectively, for 1 hr at 37° C. No biotinylation reagent was added to the third tube. The cells were washed 2×1 ml with PBS, using a microcentrifuge at 10,000 rpm for 5 min to separate the cells from the wash buffer. The cells were then lysed with 100 μl of Y-PER® (Yeast Protein Extraction Reagent) for 20 min at RT. The lysed cells were centrifuged for 5 min in a microcentrifuge at 10,000 rpm to remove any debris and then mixed 1:3 with 2× Novex Tris-Glycine SDS sample buffer and heated for 5 min at 95° C. Each sample (10 μl) was applied to a 4–20% gel. The gel was electrophoresed as described previously. The gel was incubated for 15 min with 50 ml of 50% isopropanol and then washed with 100 ml (MILLI-Q®) water for 15 min. The gel was then incubated in 20 ml HRP-labeled Streptavidin solution, at 1 mg/ml, diluted 1:250,000 in 1% BSA/PBS/05% TWEEN® 20 surfactant. The gel was washed 3×10 min with 100 ml PBS/05% TWEEN® 20 surfactant. The gel was incubated for 5 min in 10 ml SUPERSIGNAL® substrate working reagent and then washed with MILLI-Q® water for 15 sec. The gel was placed in between cellophane and exposed to X-ray film for different lengths of time. The film was developed using the Developer/Replenisher and Fixer/Replenisher solutions.

The results showed that different protein bands were observed for the cells biotinylated with the NHS-LC-Biotin compared to those biotinylated with the water-soluble Sulfo-NHS-LC-Biotin. The biotinylation of the different proteins with these reagents distinguishes between integral membrane proteins, biotinylated with the membrane soluble NHS-LC-Biotin and the cell surface proteins, biotinylated with the water soluble, but membrane insoluble, Sulfo-NHS-LC-Biotin. These results show that it is possible to distinguish between cell surface proteins and integral membrane proteins using this technique. The control experiment did not show any protein bands in response to the Streptavidin-HRP detection.

While the foregoing examples have employed the chemiluminescent substrate, luminol, and HRP, the following example, Example VII, illustrates the use of the present invention with the acridine based fluorogenic substrate, DDAO-phosphate, together with alkaline phosphatase.

Example VII

The 10–20% Tris-Glycine gel electrophoresed as described in Example 1, containing pure GST and mouse Id1:GST, Id2:GST and Id3:GST lysates, was incubated for 15 min in 50 ml of 50% isopropanol/$H_2O$ and then washed with 100 ml $H_2O$ (MILLI-Q® water) for 15 min. The gel was incubated in 20 ml rabbit anti-GST, diluted (1:1000) in 1% BSA/TBS/0.05% TWEEN® 20 surfactant, for 1 hr at RT. The gel was washed 3×10 min with 100 ml TBS/0.05% TWEEN® 20 surfactant. An alkaline phosphatase labeled secondary antibody (goat anti-rabbit antibody/alkaline phosphatase stock solution at 2 mg/ml) was diluted 1:1,000 in 1% BSA/TBS/0.05% TWEEN® 20 surfactant. The diluted antibody solution (20 ml) was added to the gel. The gel was incubated for 1 hr at RT and then washed 2×10 min with 100 ml TBS/0.05% TWEEN® 20 surfactant and 1×10 min with 10 ml TBS (pH 9.5) containing 1 mM MgCl2. The gel was incubated for 15 min at RT in 10 ml DDAO-phosphate substrate working solution [DDAO-phosphate was reconstituted at 1.25 mg/ml and then diluted 1:1,000 in TBS (pH 9.5) containing 1 mM $MgCl_2$]. The substrate was removed, and the gel was scanned using a Typhoon instrument from Amersham Pharmacia Biotech. The instrument was set at 646 nm absorbance maxima and 659 emission maxima.

All the samples, pure GST and GST lysates, were detected with this method. Thus, the example illustrates the feasibility of the invention with fluorescent substrates.

While the foregoing examples have illustrated use of the present invention in connection with interactions between proteins, it can also be extended to study the interaction of other biomolecules, such as nucleic acids. Here, the invention finds particular use in connection with assays in which interactions are detected by retardation phenomena. For example, the method can be used in the detection of DNA and RNA interactions with each other or with proteins. Such assays are practiced by a procedure in which the biomolecules of interest are incubated together in solution and then separated by gel electrophoresis. Retardation assays are based on the principle that the free biomolecule, e.g., DNA, will migrate faster than a complex, e.g., of DNA and protein. By detecting a difference in band migration in the gel the existence of an interaction can be established.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. In a method for detecting a target biomolecule directly in a polyacrylamide gel comprising (1) separating the target biomolecule from other biomolecules by electrophoresis in the gel and, while the target biomolecule remains in the gel, (2) associating the target biomolecule with an antibody having a label which is capable of providing a detectable signal, (3) removing any non-associated antibody from the gel, and (4) detecting the presence of the target biomolecule by observing a signal attributable to the presence of the labeled antibody associated with the target biomolecule; the improvement wherein, prior to associating the target biomolecule with the antibody and while the target biomolecule remains separated in the gel, (A) shrinking the gel by at least about 10% and then (B) washing the gel with water for a sufficient time to restore the gel to substantially its original size.

2. The method of claim 1, wherein shrinkage of the gel in (A) is accomplished by immersing the gel in a water miscible, aqueous extracting medium for a sufficient time to shrink the gel by at least about 10% and less than about 50%.

3. The method of claim 2, wherein shrinkage of the gel is at least about 15% and less than about 35%.

4. The method of claim 3, wherein the aqueous extracting medium comprises water and a short chain alcohol present in an amount of about 10–75% v/v.

5. The method of claim 4, wherein the alcohol is methanol, ethanol, isopropanol, or combinations thereof present in an amount of about 35–65% v/v.

6. The method of claim 5, wherein the alcohol is isopropanol present in an amount of about 50% v/v.

7. The method of claim 6, wherein shrinkage of the gel is about 20%.

8. The method of claim 5, wherein shrinkage of the gel is about 20%.

9. The method of claim 1, wherein the signal is fluorescent or luminescent.

10. The method of claim 9, wherein the label is an enzyme and the fluorescent or luminescent signal detected is generated through action of the enzyme on a substrate.

11. The method of claim 10, wherein the enzyme is alkaline phosphatase.

12. The method of claim 10, wherein the enzyme is horseradish peroxidase.

13. The method of claim 12, wherein the substrate is luminol.

14. The method of claim 10, wherein the signal detected is fluorescent.

15. The method of claim 10, wherein the signal detected is luminescent.

16. The method of claim 1, wherein the target biomolecule is a protein.

* * * * *

UNITED STATES PATENT AND TRADEMARK OFFICE
CERTIFICATE OF CORRECTION

PATENT NO. : 7,112,411 B2 Page 1 of 1
APPLICATION NO. : 10/471273
DATED : Sepetember 26, 2006
INVENTOR(S) : Desai It is certified that error appears in the above-identified patent and that said Letters Patent is hereby corrected as shown below:

In column 1, line 38, "Radioactive, calorimetric, fluorescent" should read
-- Radioactive, colorimetric, fluorescent--.

In column 5, line 30, "lystates were from" should read --lysates were from--.

In column 6, line 25, "isopropanol/H2O" should read --isopropanol/H2O--
In column 6, at line 43, immediately before the heading "Example II", add the following paragraph:

--Fig. 1 is a copy of the developed film from the assay conducted according to Example I, Lanes 1, 2 and 3 correspond to 5, 10 and 1 ng pure GST, respectively. Lanes 4 and 5 correspond to GST lysate:Id-1 (Santa Cruz Biotech) diluted 1:10 and 1:100, respectively. Lanes 6 and 7 correspond to yeast GST lysate (Pierce) diluted 1:10 and 1:100, respectively. It is to be noted that a sensitive signal with low background is obtained in this assay using GST and anti-GST, relatively large proteins.--

In column 7 line 24, "GFP/6XHis pure protein" should read -- GFP/6xHis pure protein--.
In column 7 lines 63, 65 and 67, each instance of "05%" should read --0.05%--.

In column 8 lines 3 and 4, each instance of "05%" should read --0.05%--.

Signed and Sealed this

Twenty-fourth Day of July, 2007

JON W. DUDAS
*Director of the United States Patent and Trademark Office*